(12) United States Patent
Werth

(10) Patent No.: US 7,434,779 B2
(45) Date of Patent: Oct. 14, 2008

(54) CONDUIT CLAMP

(75) Inventor: Albert A. Werth, Kewadin, MI (US)

(73) Assignee: Twin Bay Medical, Inc., Williamsburg, MI (US)

( * ) Notice: Subject to any disclaimer, the term of this patent is extended or adjusted under 35 U.S.C. 154(b) by 330 days.

(21) Appl. No.: 11/341,722

(22) Filed: Jan. 27, 2006

(65) Prior Publication Data

US 2006/0169934 A1    Aug. 3, 2006

Related U.S. Application Data

(60) Provisional application No. 60/648,089, filed on Jan. 28, 2005.

(51) Int. Cl.
*F16K 7/04* (2006.01)
(52) U.S. Cl. .............. 251/10; 251/4; 604/250
(58) Field of Classification Search .......... 251/4, 251/9, 10; 604/250
See application file for complete search history.

(56) References Cited

U.S. PATENT DOCUMENTS

| | | | |
|---|---|---|---|
| 850,731 A | 4/1907 | Christensen et al. | |
| 3,915,167 A | 10/1975 | Waterman | 604/250 |
| 4,049,301 A | 9/1977 | Schenk | 292/113 |
| 4,247,076 A | 1/1981 | Larkin | 251/7 |
| 4,588,160 A | 5/1986 | Flynn et al. | 251/10 |
| 4,736,925 A * | 4/1988 | Kamstrup-Larsen et al. | 251/10 |
| 4,944,485 A * | 7/1990 | Daoud et al. | 251/9 |
| 5,203,056 A | 4/1993 | Funk et al. | 24/543 |
| 5,271,649 A | 12/1993 | Gromotka | 292/113 |
| 5,318,546 A | 6/1994 | Bierman | 604/34 |
| 6,113,062 A | 9/2000 | Schnell et al. | 251/10 |
| 6,173,926 B1 | 1/2001 | Elvegaard | 248/74.1 |
| 6,234,448 B1 | 5/2001 | Porat | 251/10 |
| 6,261,254 B1 | 7/2001 | Baron et al. | 602/323 |
| 6,390,721 B1 | 5/2002 | Wilson, II et al. | 403/312 |
| 6,422,529 B1 | 7/2002 | Adelberg | 251/6 |
| 2003/0188401 A1 | 10/2003 | Huang | 24/193 |

OTHER PUBLICATIONS

International Search Report and Written Opinion, dated Nov. 23, 2007, from the corresponding International Application No. PCT/US06/03074.
International Preliminary Report on Patentability, dated Dec. 11, 2007, from the corresponding International Application No. PCT/US06/03074.

\* cited by examiner

*Primary Examiner*—John K. Fristoe, Jr.
(74) *Attorney, Agent, or Firm*—Young Basile

(57) ABSTRACT

A conduit clamp has an upper member and a lower member selectively connectable around a flexible tube. The upper member and lower member has interconnecting pivot points for pivotally connecting to each other. The lower member has a pair of opposing sidewalls with rocker arms integrally formed therein for receiving and moving a locking protuberance extending on outer surfaces of the upper member as the conduit is depressed into a locked and closed position. The rocker arms are flexible to allow the locking protuberances to move in and out of gaps formed around the rocker arms for closing and opening the conduit clamp. The upper member has a pair of sidewalls and a lower extending projection therebetween. The extending projection closes the pathway in the flexible tube as the conduit clamp moves to a closed position.

17 Claims, 4 Drawing Sheets

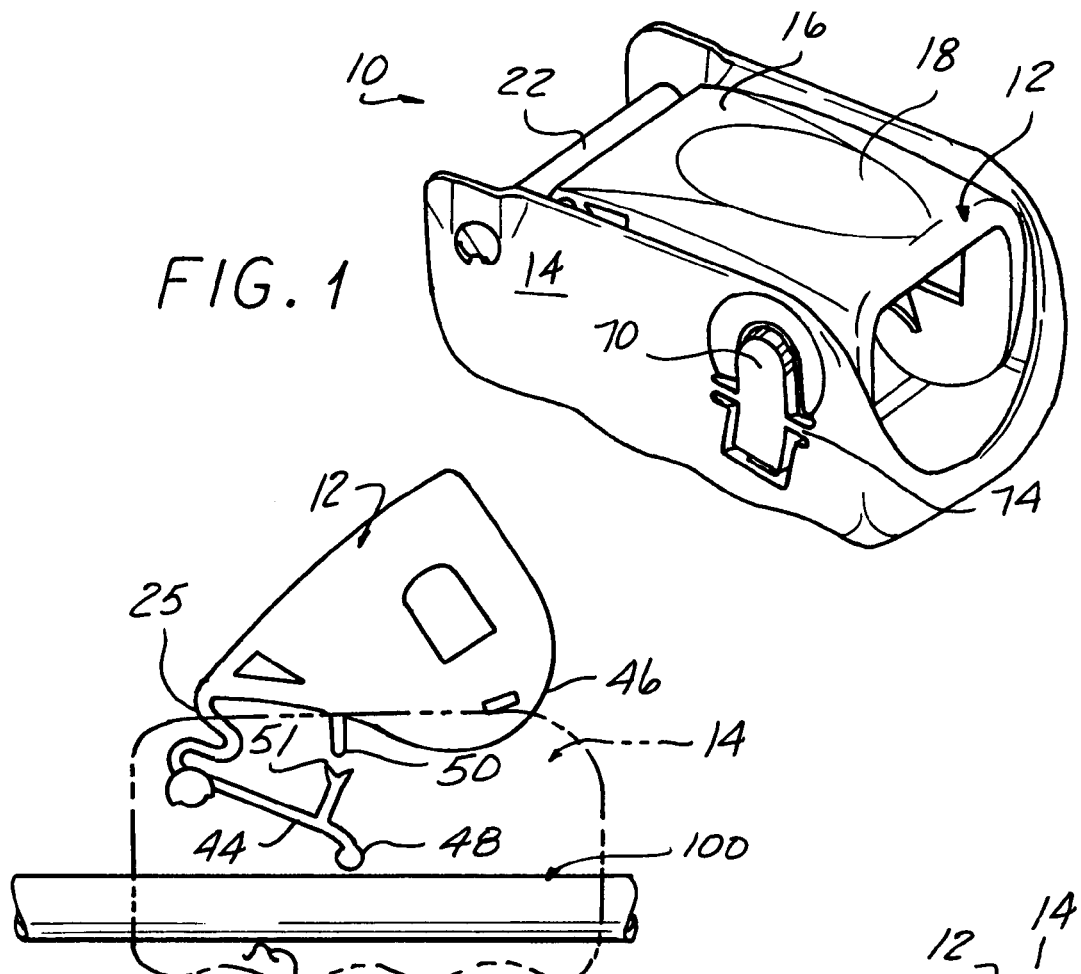
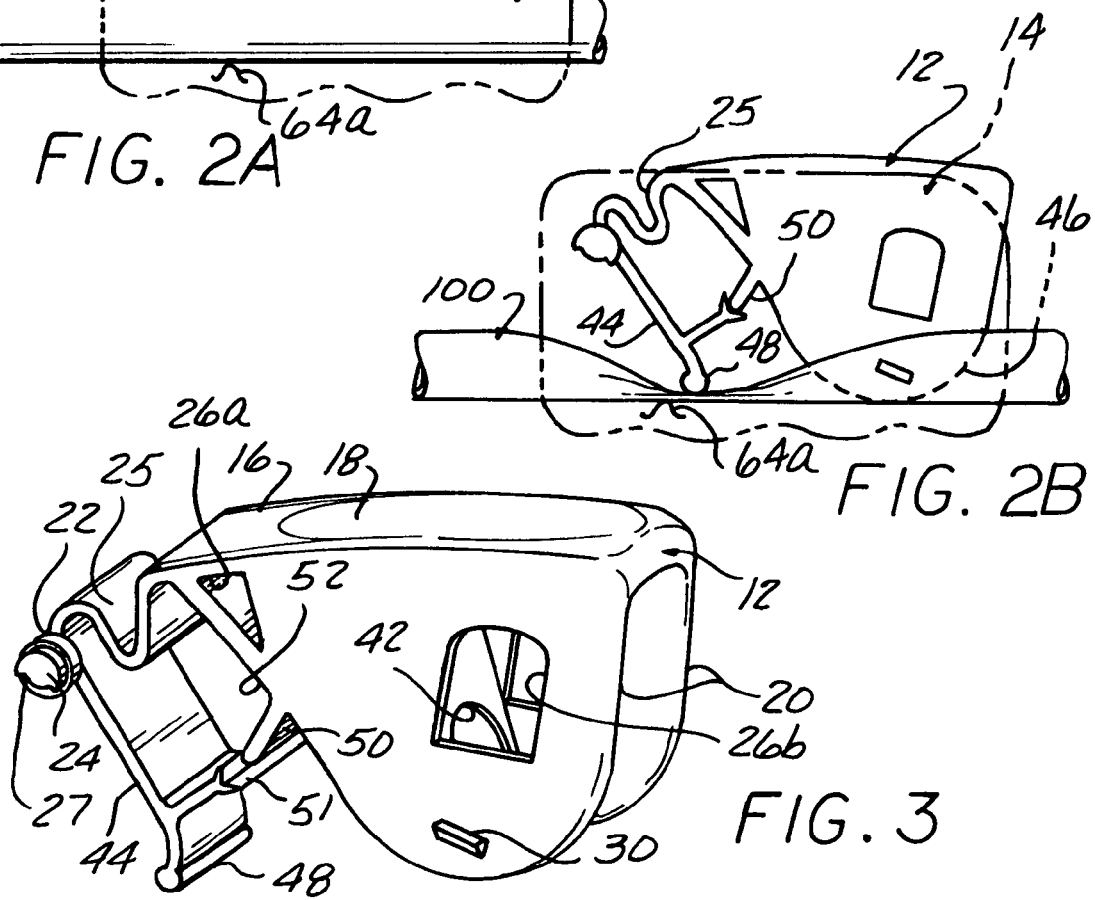

CONDUIT CLAMP

This application claims priority of U.S. provisional application Ser. No. 60/648,089 filed on Jan. 28, 2005.

FIELD OF THE INVENTION

This invention relates to a conduit clamp for selectively opening and closing a pathway in resilient tube.

BACKGROUND OF THE INVENTION

Flexible tubing made of plastic or rubber is widely used in the medical, pharmaceutical, biopharmaceutical, food and beverage, and other laboratory environments. In many instances during the conveying of fluids through the flexible tubing, it is desirable to close and stop the flow of the fluid through the tube. Conduit clamps in the prior art contained undesirable features. Conduit clamps in the prior art have outer body features with sharp edges, these have the potential for snags, scratches or punctures. This may cause plastic bio-bags to be damaged. The sharp corners can cut or damage the bags in transit. Many clamps of the prior art require that the clamp be installed onto the tube only at the ends which required the clamp being threaded from the-end of the tube to its desired location. This procedure can only occur before the tube is assembled to the solution container and not when the tube is completely assembled in place. Further, when the prior art clamp fails to operate properly or is damaged during use the tubing must be removed from the fittings to replace clamp. Other undesirable features include difficulty to lock the clamp into the closed position and difficulty to pry the clamp open again. The prior art clamp also contains ratchet type closures that have a tendency for untimely or unwanted release. It is therefore desirable to provide a conduit clamp that can be installed onto a flexible tube at anytime and easily opened and closed with only a push button finger pressure without unwanted openings.

SUMMARY OF THE INVENTION

It is the intent of the present invention to address the aforementioned concerns. The present invention is a conduit clamp for selectively restricting or closing a fluid path in a flexible tube. The conduit clamp is a two-piece construction having an upper member and a lower member pivotally connected together at a pivot point for moving the upper member between an open and closed position. The upper and lower members are separable and connectable at the pivot point for assembly and disassembly of the conduit clamp on the tube. The lower member forms a through trough for receiving a segment of the tube therein. The upper member has a center projection for closing the fluid path of the tube when the upper member is pivotally moved to the closed position.

In another aspect of the invention the upper member and lower member have means for locking the upper member in the closed position.

In yet another aspect of the invention, the means for locking the upper member in the open or closed positions include a rocker arm integrally formed in side walls of the lower member. The rocker arm is surrounded by a gap along most of its periphery and a protuberance on an exterior surface of the upper member for disposition in a portion of the gap when the upper member is locked in the open or closed positions. The rocker arm also provides means for releasing the upper member from the closed and locked position, in that the rocker arm can be manually depressed at one end to flex the opposing end of the rocker arm to release the protuberance from the gap.

BRIEF DESCRIPTION OF THE DRAWINGS

The description herein makes reference to the accompanying drawings wherein like reference numerals refer to like parts throughout the several views, and wherein:

FIG. 1 is a perspective view of the conduit clamp of the present invention with an upper and lower member connected together in a closed position;

FIG. 2a is a side elevational view of the conduit clamp in an open position showing a portion of the upper member pivoted away from a tube;

FIG. 2b is a side elevational view of the conduit clamp in a closed position showing the upper member clamped down and sealing a pathway in the-tube;

FIG. 3 is a perspective view showing a side wall and top portion of the upper member;

DESCRIPTION OF THE PREFERRED EMBODIMENT

Figure 4:
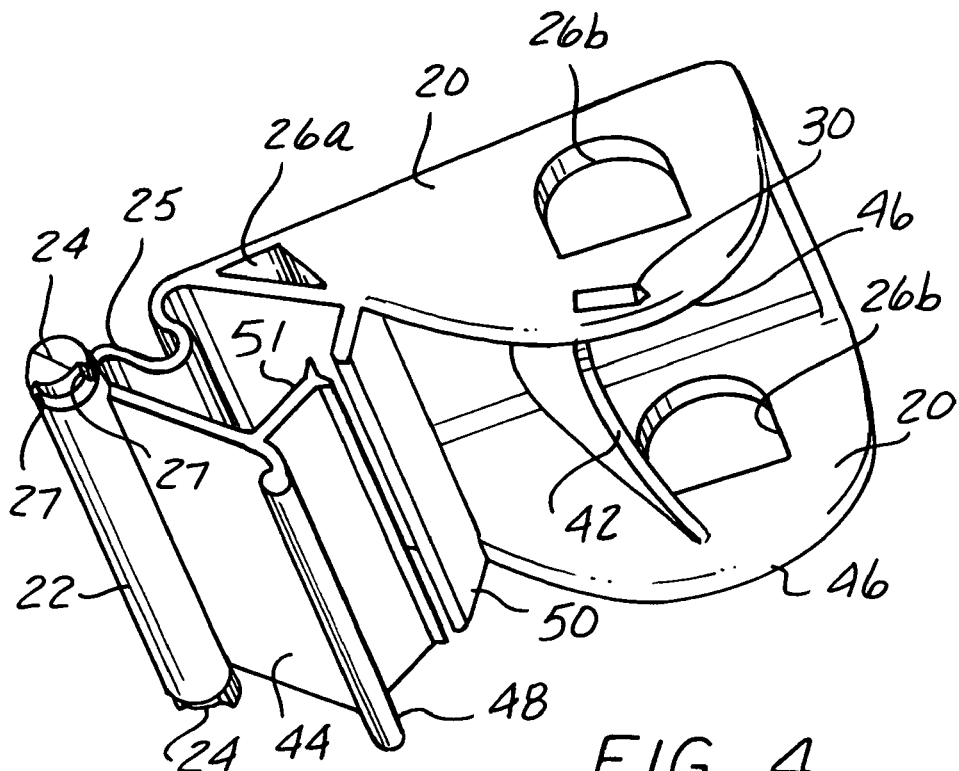
FIG. 4 is a perspective view showing the bottom portion of the upper member.

Looking at FIGS. 1-10, a conduit clamp 10 is provided for pinching and/or closing the fluid path of a flexible tube to prevent any fluid from flowing through the tube 100 in a manifold system, from or to a bio-bag, or a patient. Although the conduit clamp of the present invention can be used in various environments, the conduit clamp 10 is most beneficial in the medical or pharmaceutical field for selectively controlling the flow of fluid from or to the patient. The clamp 10 of the present invention is made of a non-metallic material and preferably made of an FDA (Food and Drug Administration) approved PVDF, polypropylene, polysulfone, silicon, TPE, TPR, etc. The clamp 10 features a complete outer body with no sharp edges eliminating the potential of snags, scratches, or punctures. The unique locking mechanism is fully encapsulated to guard against untimely or unwanted release. The clamp has a press down locking system and a side release mechanism allowing for secure and single handed operation and installation. This high-tech design allows for complete flow stoppage and can be installed over the tube in the normal fashion or assembled after the tube is already in formation.

The assembled conduit clamp is shown in FIGS. 1, 2a, 2b, 9a, and 9b. The conduit clamp 10 of the present invention has a separable upper member 12 and lower member 14 which can selectively be placed around a tube 100 and then connected together either before or after the assembly of the tube. 100 in its environment. The upper member 12 and lower member 14 pivotally connect to each other at one end to provide a jaw-like movement of the clamp 10 as it opens and closes.

The upper member 12 has essentially a U-shaped configuration with an upper surface 16 and two side walls 20. The exposed upper surface 16 of the upper member 12 has a shallow impression 18 defining a space for placement of a finger or thumb when closing the conduit clamp 10. The upper member 12 has a pivot end 22 with a cylindrical formation 22. The pivot end 22 is the point of connection of the upper and lower members 12, 14 respectively. The cylindrical pivot end 22 is integrally connected to the upper surface 16 by an integral undulated portion 25 that provides strength to the upper member 12. The undulated portion 25 allows the upper member 12 to move forward when heavier tubing 100 is being clamped and closed. The undulated portion 25 allows the upper member 12 to self-adjust to provide a complete closing of the fluid path even when the walls of the tube 100 are thick.

Each lateral end 24 of the cylindrical pivot end 22 is adjacent to a side wall 20. A conical-shaped or cylindrical-shaped lobe 24 is formed on each end of the cylindrical pivot end 22. The lobes 24 extend laterally beyond the side walls 20 for connection to the lower member 14 as discussed hereinafter.

The lobes 24 have a cutout 27 to define the range of pivotal rotation allowed for the upper member 12 relative to the lower member 14. The lower member 14, as will be discussed hereinafter, has corresponding apertures 63 sized for lockingly receiving the lobes 24 therein. The apertures 63 will preferably have a small projection 65 extending into the apertures 63. The projection 65 moves within the boundaries of the cutout 27 in the lobes 24 to limit the pivotal rotation of the upper member 12 relative to the lower member 14. The lower member 14 is shown in phantom on FIGS. 2a, 2b to show the relationship of the upper member to the tube 100, when the clamp 10 is in the opened (FIG. 2a) and closed (FIG. 2b) position.

Referring to FIG. 3, side walls 20 are adjacent to and contiguously formed with the upper surface 16. Each side wall 20 is a mirror image of the other, and therefore only one side wall 20 will be discussed. The side wall 20 of the upper member 12 has an open configuration defined by a pair of windows 26a, 26b formed therein and spaced from each other A first window 26a provides an access for eliminating the steel portions of the mold during the manufacturing process. The second window 26b provides a cutout for depression of a rocker arm 70 on the lower member 14. The window 26b is positioned in wall 20 to be adjacent the rocker arm 70 when the clamp 10 is in the closed position. Proximate to the lower edge of the exterior of each side wall 20 is a protuberance 30 laterally extending therefrom. The protuberance 30 is spaced from the pivot point 22. The protuberances 30 on each of the side walls 20 are positioned and formed to slide against the rocker arm 70 formed in the lower member 14 and to lock in place in an opening 72b formed below the rocker arm 70 as will be discussed hereinafter.

Figure 9A:
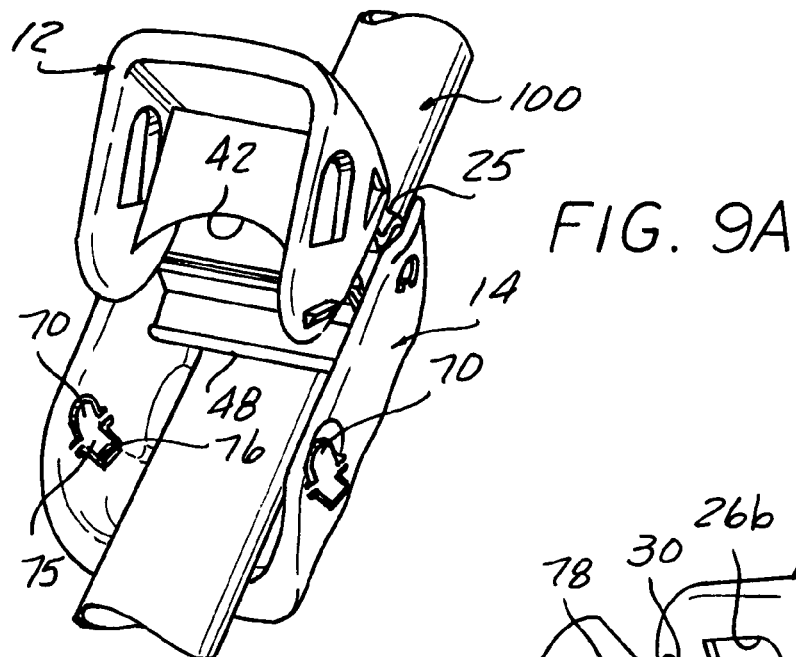
FIGS. 9a and 9b are perspective views of the conduit clamp with a tube therein in an open position.
Figure 9B:
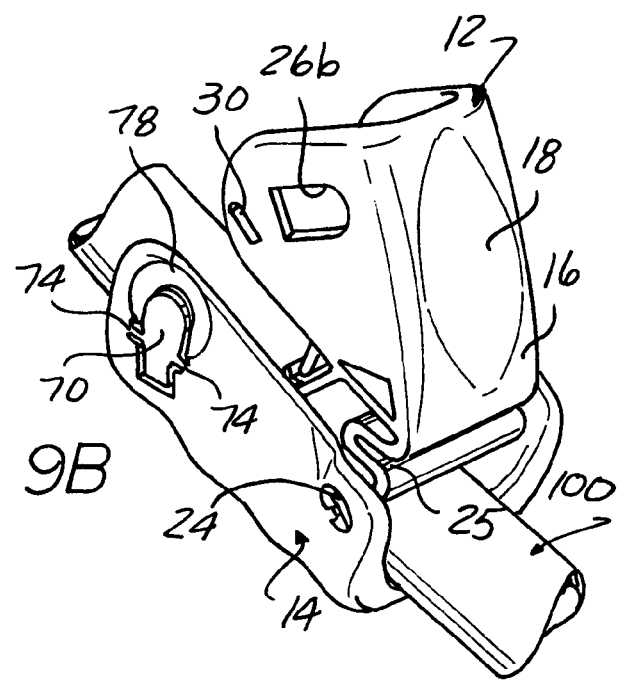
Figure 10:
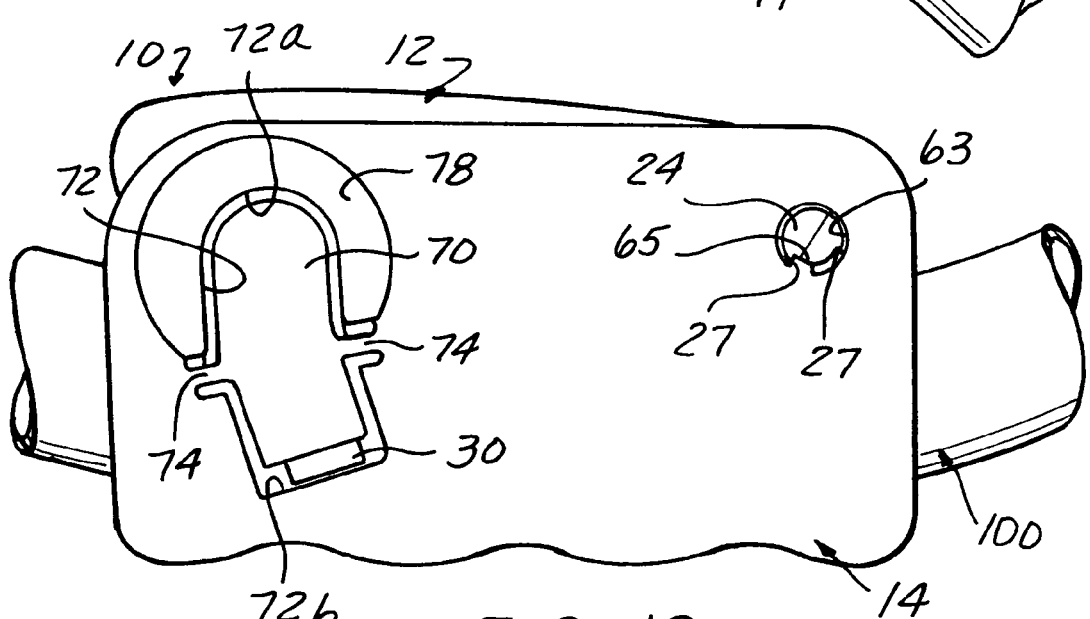
FIG. 10 is a side elevational view of the conduit clamp in the closed position.

Looking at FIG. 4, a rib 42 extends laterally between the two side walls 20. The rib 42 provides strength to the side walls 20 so that the side walls 20 do not flex outwardly or inwardly when the upper member 12 is manually depressed when closing the conduit clamp 10. The rib 42 between the two side walls 20 has an arch formation to provide clearance for the tube 100, as shown in FIG. 9a.

A center projection 44 integrally extends from the pivot end 22 and behind the side walls 20. The projection 44 preferably has the same width as the pivot end 22. The projection 44 partially extends at least as far as the lower surface 46 of each side wall 20, in order to fully close the pathway in the tube 100 when the clamp 10 is in the closed and locked position (see FIG. 2b). The projection 44 terminates and forms a laterally extending cylindrical portion 48 at the free end of the projection 44 to prevent a sharp edge cutting into the tube 100. The cylindrical portion 48 of the projection 44 pinches the tube 100 closed and locked when the conduit clamp 10 is in the closed position. The projection 44 and its cylindrical edge 48 are not connected to the side walls 20 so that the projection 44 and its associated cylindrical portion 48 can flex slightly vertically relative to the two side walls 20 when the clamp is closed.

A C-spring 50, defined as a curved section of material has one end connected to the back wall 52 adjacent the rear edge of the side walls 20. The C-spring 50 allows flexing when a higher load to be applied to the upper surface 16 of the upper member 12 to close and lock the conduit clamp 10. A tube with a thick wall requires a higher load to be applied to the upper surface 16 of the upper member 12 to close the clamp 10. The C-spring 50 allows the undulated portion 25 to stretch or elongate when the upper member 12 has to adjust to close the pathway of the tube 100, especially a tube with a thick wall. The C-spring 50 also provides resiliency to the projection 44 when an upper extending appendage 51 on the projection 44 contacts the C-spring 50, as shown in FIG. 2b. As can be seen, appendage 51 and C-spring 50 contact each other when the upper member 12 pivots toward closing the clamp 10.

Figure 5:
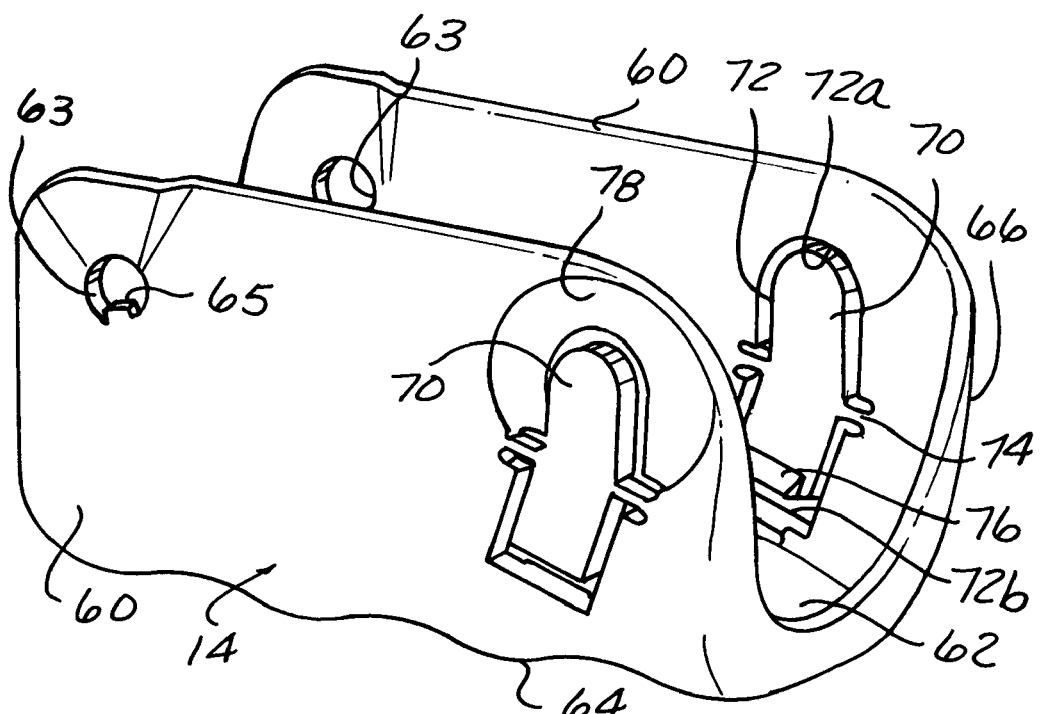
FIG. 5 is a perspective view of the lower member.
Figure 6:
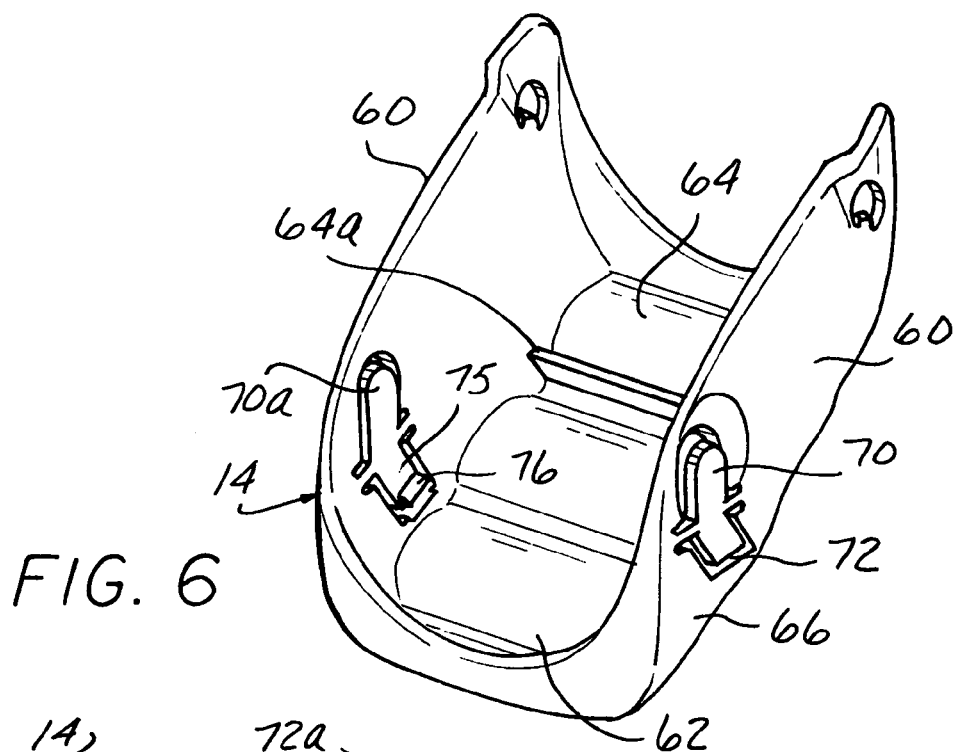
FIG. 6 is another perspective view of the lower member illustrating certain interior features.
Figure 7:
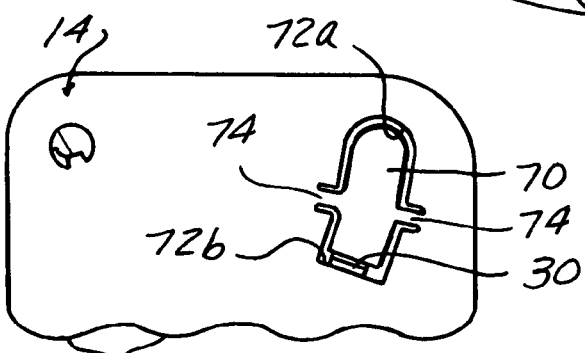
FIG. 7 is a side elevational view of the lower member illustrating certain exterior features.

FIGS. 5 and 6 show the lower member 14 of the conduit clamp 10. The lower member 14 has a through trough or U-shaped configuration with a pair of side walls 60 meeting with a bottom surface 62. The bottom surface 62 of the lower member 14 includes at least one laterally extending bump 64 protruding upward between the two side walls 60 for cooperating with the cylindrical portion 48 of the center projection 44 to close the fluid flow in the tube 100. Multiple bumps 64 may also be provided as finger grips. In the preferred embodiment, one of the bumps may be formed as a raised bar 64a traversing the inner bottom surface 62 of the lower member 14. The raised bar 64a is positioned to slightly offset the cylindrical portion 48 of the upper member 12 when the clamp 10 is in the closed position to provide space for the tube material.

Each side wall 60 is a mirror image of the other side wall 60, and therefore only one side wall 60 will be discussed. Proximate to a forward end 66 of the side wall 60 a rocker arm 70 is formed therein. The rocker arm 70 is cut directly into each side wall 60 leaving a gap/opening 72 around the rocker arm 70 except for the connecting flanges 74 which connect a mid-section of the rocker arm 70 to the material of the side walls 60. The rocker arm 70 pivots about the connecting flanges 74. Manual pressure on either end of the rocker arm 70 will cause the opposite end to flex outward relative to the side walls 60. The gap/opening 72 is sized at the upper end 72a and lower end 72b to accommodate the protuberances 30 on the upper member 12.

The rocker arm 70 defines the path of the protuberance 30 relative to the lower member 14 when downward pressure is applied to the upper member 12 to close the clamp or when the clamp is being opened. Looking first at FIG. 7, the shape of the rocker arm 70 has a downward arcuate curved path which coincides with the arcuate path of the movement of the protuberance 30 as the upper member 12 pivots relative to the lower member 14.

Figure 8A:
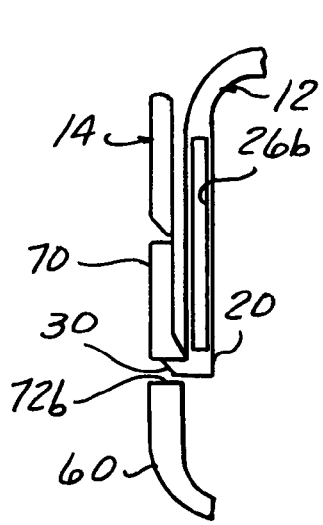
FIGS. 8a-8c are schematic views showing various movements of portions of the conduit clamp as it opens from a closed position.
Figure 8B:
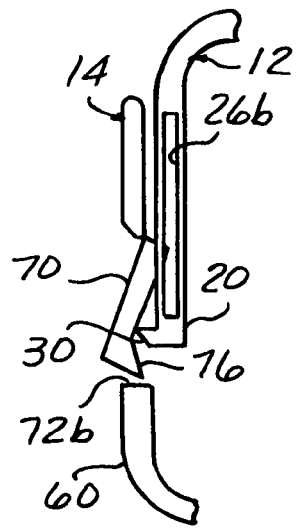
Figure 8C:
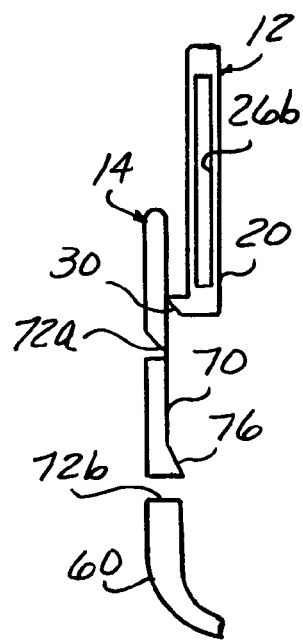

When the conduit clamp 10 is in the open position, the protuberance 30 is held in or above the upper gap 72a as shown in FIG. 8c. As downward pressure is applied to the upper member 12, the protuberance 30 slides along the inner surface 75 of the rocker arm 70. The inner surface of the rocker arm 70 may include a lip 76 at the bottom edge of the rocker arm 70 extending inwardly, as shown in FIG. 6 and 9a.

The lip 76 keeps the clamp in the unlocked position until added manual pressure is placed on the upper member 12. Further, pressure on the upper member 12 moves the protuberance 30 over the lip 76 so that the protuberance 30 snaps into the lower gap 72b to lock the conduit clamp 10 in the closed position.

To open the conduit clamp 10 from a closed position, the operator manually depresses the upper portion 70a of the rocker arm 70. The upper portion 70a of the rocker arm 70 is positioned adjacent the window 26b when the conduit clamp 10 is closed or locked to allow for full depression of the upper rocker arm 70. As can be seen in the drawings, the outer surface of the lower member 14 has a depression 78 surrounding the upper portion 70a of the rocker arm 70 to facilitate the manual depression of the upper portion 70a of the rocker arm 70.

FIGS. 8a-8b show the movement of a wall 20 of the upper member 12 relative to a wall 60 of the lower member 14 as the clamp 10 moves from the closed and locked position to the open position. In FIG. 8a the conduit clamp 10 is in the closed and locked position showing the protuberance 30 locked in opening 72b. The lip 76 secures the protuberance 30 in the opening 72b until the rocker arm 70 is manually pivoted, as shown in FIG. 8b. When the rocker arm 70 is pivoted, an upper portion of the rocker arm is pivoted into a portion of the window 26b (FIG. 8b). The protuberance 30 is then release from the opening 72b, and can slide past the lip 76 to move the upper member 16 upwardly as shown in FIG. 8c to open the conduit clamp 10.

The upper member 12 can be connected to the lower member 14 either before the conduit clamp 10 is threaded onto the tube 100, or the tube 100 may be placed in the trough, between the side walls 60 of the lower member 14 before the upper member 12 is connected to the lower member 14. In either case, the upper member 12 is connected to the lower member 14 by snapping the lobes 24 of the upper member 12 into the apertures 63 of the lower member to form the pivot end. The upper member 12 can be separated from the lower member 14 by opening the clamp 10 and flexing the side walls 60 of the lower member 14 to remove the lobes 24 from apertures 63.

The clamp 10 provides complete fluid stoppage and can be installed on or over tubing or finished assemblies with a single hand installation for ease of operation. The unique top locking mechanism with a side release mechanism prevents unwanted openings. The clamp 10 also provides an internal ratchet mechanism that meters fluid flow, and has a high degree of leverage to accommodate varied durometer tubing. The clamp 10 has no sharp edges or corners, thereby preventing punctures and ruptures of the tube 10.

The clamp 10 of the present invention is fully autoclavable and sterilizable and meets all USP Class VI criteria. The tube clamps of the present invention have been physically tested to meet the most demanding applications. Typical applications for the conduit clamp includes biopharmaceutical manufacturing, pharmaceutical processes, peristaltic pump sets, drug delivery and discovery, medical systems, laboratory functions, and other assemblies and tubing sets.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

The invention claimed is:

1. A conduit clamp for selectively restricting or closing a fluid path inside a hollow tube, the conduit clamp comprising:
a two-piece construction having an upper member and a lower member pivotally connected together at a pivot point for moving the upper member between an opened and closed position, said upper a member and lower member separable at the pivot point for assembly and disassembly on the tube, said lower member forming a through trough for receiving a portion of the tube therein, said upper member having a center projection for restricting or closing the fluid path of the tube when the upper member is pivotally moved to the closed position, wherein the upper member has a pair of side walls contiguously formed with an upper surface, the pair of side walls configured for being disposed within the trough of the lower member when the upper member is in the closed position and wherein the pair of side walls each have a protuberance at a predetermined location extending from exterior surfaces of the pair of side walls, wherein the trough of the lower member is formed by a pair of side walls, wherein a side wall of the upper member is adjacent a side wall of the lower member when the upper member is in the closed position, and wherein the pair of side walls of the lower member has means for receiving a portion of the protuberances when the upper member is in the closed position, wherein the means for receiving a portion of the protuberances in the upper member includes a window in each sidewall of the upper member.

2. The conduit clamp of claim 1, wherein the pivot point has means for restricting the pivotal movement of the upper member relative to the lower member.

3. The conduit clamp of claim 1, wherein each of the pair of side walls in the lower member have a rocker arm integrally formed therein, the rocker arm defining a path for the protuberance when the upper member moves between the open and closed positions.

4. The conduit clamp of claim 1, wherein the trough of the lower member has an inner bottom surface integrally formed between the pair of side walls of the lower member, said inner bottom surface having a raised bar traversing the inner bottom surface positioned to correspond with the center projection.

5. The conduit clamp of claim 4, wherein the raised bar slightly offsets the center projection to provide space for the tube material when the clamp is in a closed position.

6. The conduit clamp of claim 1, further comprising means for adjusting the movement of the upper member when closing the pathway of the tube.

7. A conduit clamp for selectively restricting or closing a fluid path inside a hollow tube, the conduit clamp comprising:
a two-piece construction having an upper member and a lower member pivotally connected together at a pivot point for moving the upper member between an opened and closed position, said upper a member and lower member separable at the pivot point for assembly and disassembly on the tube, said lower member forming a through trough for receiving a portion of the tube therein, said upper member having a center projection for restricting or closing the fluid path of the tube when the upper member is pivotally moved to the closed position, wherein the upper member has a pair of side walls contiguously formed with an upper surface, the pair of side walls configured being disposed within the trough of the lower member when the upper member is in the closed position and wherein the air of side walls each having a protuberance at a predetermined locating extending from exterior surfaces of the pair of side walls, wherein the trough of the lower member is formed by a pair of side walls, wherein a side wall of the upper member is adjacent a side wall of the lower member when the upper member is in the closed position, wherein the pair of side walls of the lower member has means for receiving a portion of the protuberances when the upper member is in the closed position and, wherein each of the pair of side walls in the lower member have a rocker arm integrally formed therein, the rocker arm defining a path for the protuberance when the upper member moves between the open and closed positions, wherein a rocker is integrally connected to each side wall in the lower member by connecting flanges located in a mid-section of the rocker arm and having a gap around the remaining portion of the rocker arm for allowing the rocker to flex relative to the side wall of the lower member.

8. The conduit clamp of claim 7, wherein the gap has an upper gap portion and a lower gap portion positioned for receiving the protuberance therein.

9. The conduit clamp of claim 7, wherein the rocker arm has an inner surface and bottom edge and wherein the rocker arm has a lip formed at the bottom edge of the inner surface for maintaining the upper member in the closed and a locked position.

10. The conduit clamp of claim 9, wherein the side walls of the upper member have windows therein positioned adjacent the rocker arms when the upper member is in the closed position for allowing full deflection of the rocker arm, when the upper member is in the closed position and locked position.

11. As conduit clamp for selectively restricting or closing a fluid path inside a hollow tube, the conduit clamp comprising:
a two-piece construction having an upper member and a lower member pivotally connected together at a pivot point for moving the upper member between an opened and closed position, said upper a member and lower member separable at the pivot point for assembly and disassembly on the tube, said lower member forming a through trough for receiving a portion of the tube therein, said upper member having a center projection for restricting or closing the fluid path of the tube when the upper member is pivotally moved to the closed position, wherein the upper member has a pair of side walls contiguously formed with an upper surface, the pair of side walls configured being disposed within the trough of the lower member when the upper member is in the closed position and wherein the pair of side walls each have a protuberance at a predetermined locating extending from exterior surfaces of the pair of side walls, wherein the pivot point and the pair of side walls of the upper member are separated by an undulated portion for allowing the upper member to self-adjust when closing the fluid path of the tube.

12. The conduit clamp of claim 11, further comprising a C-spring integrally formed on the upper member for allowing the undulating portion to elongate when the upper member self-adjusts.

13. The conduit clamp of claim 11 further comprising: a spring member on the upper member, positioned between the pivot point and side walls of the upper member for flexing during a load applied to the upper surface.

14. The conduit clamp of claim 11 having a top locking mechanism and a side release mechanism.

15. The conduit clamp of claim 14, wherein the locking mechanism is encapsulated within the clamp.

16. A conduit clamp for selectively restricting or closing a fluid path inside a hollow tube, the conduit clamp comprising:
a two-piece construction having an upper member and a lower member pivotally connected together at a pivot point for moving the upper member between an opened and closed position, said upper a member and lower member separable at the pivot point for assembly and disassembly on the tube, said lower member forming a through trough for receiving a portion of the tube therein, said upper member having a center projection for restricting or closing the fluid path of the tube when the upper member is pivotally moved to the closed position; and
means for adjusting the movement of the upper member when closing the pathway of the tube, wherein the adjusting means includes an undulating portion positioned between the pivot point and an opposing end of the upper member.

17. The conduit clamp of claim 16, wherein the adjusting means further includes a C-spring integrally formed on the upper member.

* * * * *